United States Patent
Prasad et al.

[19]

[11] Patent Number: 6,039,569
[45] Date of Patent: Mar. 21, 2000

[54] FIBER-REINFORCED DENTAL STRUCTURES AND METHOD OF MANUFACTURE THEREOF

[75] Inventors: Arun Prasad, Cheshire; Ajit Karmaker, Wallingford; Elie Zammarieh, Milford; Grant P. Day, Cheshire, all of Conn.

[73] Assignee: Jeneric/Pentron Incorporated, Wallingford, Conn.

[21] Appl. No.: 09/130,911

[22] Filed: Aug. 7, 1998

Related U.S. Application Data

[60] Provisional application No. 60/055,590, Aug. 12, 1997.

[51] Int. Cl.[7] .................. A61C 13/12; A61C 13/225; A61C 5/08
[52] U.S. Cl. .................................................. 433/180
[58] Field of Search ..................... 433/180, 181, 433/182, 183, 215, 218, 219

[56] References Cited

U.S. PATENT DOCUMENTS

| | | |
|---|---|---|
| 4,144,645 | 3/1979 | Marshall . |
| 4,346,750 | 8/1982 | Nemethy . |
| 4,380,435 | 4/1983 | Raeder et al. . |
| 4,457,714 | 7/1984 | Klein . |
| 4,459,111 | 7/1984 | Valen . |
| 4,543,064 | 9/1985 | Wolf . |
| 4,717,341 | 1/1988 | Goldberg et al. . |
| 4,758,162 | 7/1988 | Dobbs . |
| 4,764,116 | 8/1988 | Shoher et al. . |
| 4,820,157 | 4/1989 | Salvo . |
| 4,838,790 | 6/1989 | Koller .................................. 433/218 X |
| 4,846,718 | 7/1989 | Rieger .................................. 433/218 X |
| 4,877,400 | 10/1989 | Holsclaw . |
| 4,894,012 | 1/1990 | Goldberg et al. . |
| 4,906,191 | 3/1990 | Söderberg . |
| 4,950,162 | 8/1990 | Korber et al. . |
| 5,000,687 | 3/1991 | Yarovesky et al. . |
| 5,052,928 | 10/1991 | Andersson . |
| 5,074,791 | 12/1991 | Shoher et al. . |
| 5,171,147 | 12/1992 | Burgess . |
| 5,194,001 | 3/1993 | Salvo . |
| 5,234,343 | 8/1993 | Shoher et al. ...................... 433/218 X |
| 5,575,651 | 11/1996 | Weissman . |
| 5,772,438 | 6/1998 | Deom . |
| 5,839,900 | 11/1998 | Billet et al. .............................. 433/218 |
| 5,921,778 | 7/1999 | Karmaker et al. .................. 433/219 X |

FOREIGN PATENT DOCUMENTS

| | | |
|---|---|---|
| PCT/FR94/01119 | 3/1995 | WIPO . |

*Primary Examiner*—Nicholas D. Lucchesi
*Attorney, Agent, or Firm*—Cantor Colburn LLP

[57] ABSTRACT

The present invention relates to unique dental structures such as bridges and crowns. The bridge comprises a structural component such as a fiber reinforced polymeric matrix bar disposed within interproximal cavities located in the distal occlusal surface of the mesial abutment tooth and the mesial occlusal surface of the distal abutment tooth. A structural wrap and/or occlusal strip comprising fibers embedded within a polymeric matrix can also be employed where the wrap is attached to one or both abutment teeth and one or both sides of the structural component. The occlusal strip is attached to the occlusal surface of both of the abutment teeth, spans the edentulous area, and is attached to the top surface of the structural component. Meanwhile, the crown comprises a wrap disposed around and adhered to a damaged natural tooth and may have an occlusal strip adhered to the occlusal surface of the natural tooth where the wrap is disposed around the edge of the occlusal strip. In both embodiments a pontic can then be built up around the structures to form the final product.

47 Claims, 7 Drawing Sheets

FIBER-REINFORCED DENTAL STRUCTURES AND METHOD OF MANUFACTURE THEREOF

CROSS REFERENCE TO RELATED APPLICATIONS

This application claims priority to Provisional U.S. Application No. 60/055,590 (hereby incorporated by reference).

BACKGROUND OF THE INVENTION

1. Field of the Invention

The present invention relates to dental restoration devices and methods of manufacture thereof. In particular, this invention relates to dental bridges comprising at least one fiber-reinforced structural component and a method of manufacture thereof.

2. Brief Description of the Related Art

In the dental arts, a bridge is a device for the restoration and replacement of one or more natural teeth, it replaces at least one missing tooth and is supported on either side by the remaining teeth. A bridge generally comprises a pontic for replacement of the missing tooth, and a connector which connects the pontic to a retaining member such as a crown formed on an abutment tooth adjacent the pontic. By their nature, bridges must be aesthetic, as well as strong, in order to withstand forces generated by mastification of various types of foods and to maintain the positions of the abutting teeth. Not surprisingly, construction of a dental bridge is often a time consuming, involved, and complex process requiring multiple steps. Accordingly, a number of bridge designs are disclosed in the prior art which are intended to either enhance strength or ease of preparation. For example, U.S. Pat. No. 5,074,791 discloses a bridge comprising a pre-formed pontic, which simplifies preparation. The so-called winged bridge disclosed in U.S. Pat. No. 5,000,687 is designed to enhance bridge strength. U.S. Pat. No. 4,877,400 to Holsclaw discloses a dental bridge comprising a metal pontic rod that is opaqued and installed in refractory model notches. The metal pontic rod and abutment teeth are coated with a porcelain mix and cured. U.S. Pat. No. 4,758,162 to Dobbs discloses a dental bridge comprising a wax occlusal bar and at least one removable wax pontic.

A prefabricated dental bridge in U.S. Pat. No. 4,764,116 to Schoher et al. discloses a prefabricated pontic having a framework that is adjustable by use of a plurality of pliable metal members which interconnect for an open skeleton framework. U.S. Pat. No. 4,457,714 to Klein discloses a prefabricated dental bridge comprising a vertically-orientated pontic element and a pair of horizontally-extending bars disposed on opposite sides of the pontic element.

While suitable for their intended purposes, there still remains a need for dental structures which are aesthetically pleasing, strong and simple for the dentist or dental technician to prepare.

SUMMARY OF THE INVENTION

The above-discussed and other problems and deficiencies of the prior art are overcome or alleviated by the structures and method of preparation therefor of the present invention. The process comprises the steps of: forming opposing first and second interproximal cavities in the distal occlusal portion of the mesial abutment tooth and in the mesial occlusal portion of the distal abutment tooth, respectively; preparing at least one structural component comprising reinforcing fibers embedded within a polymeric matrix, said component having a sufficient size and geometry to span in and between said first interproximal cavity and said second interproximal cavity; disposing the structural component in and between the first and second interproximal cavities; and attaching an occlusal strip to the occlusal portion of one of said abutment teeth and to said structural component, said occlusal strip comprising second reinforcing fibers embedded within a second polymeric matrix.

The dental bridge of the present invention is for replacing at least one missing natural tooth in which first and second abutment teeth have opposing first and second interproximal cavities in the distal portion of the occlusal surface of the mesial abutment tooth and in the mesial occlusal surface of the distal abutment tooth, respectively. This dental bridge comprises: at least one structural component comprising reinforcing fibers embedded within a polymeric matrix, said structural component formed to span in and between the first and second interproximal cavities of the abutment teeth; and a wrap having second reinforcing fibers embedded within a second polymeric matrix, said wrap attached to said structural component and at least one of said abutment teeth.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES.

DESCRIPTION OF THE PREFERRED EMBODIMENT

The present invention comprises a method for replacing one or more missing natural teeth using abutment teeth as supports for a reinforcing structural component, which spans the abutment teeth.

The structural component is a fiber-reinforced composite material comprising reinforcing fibers within a polymeric matrix. The fibers of the structural component preferably take the form of long, unidirectional, continuous filaments which are preferably at least partially aligned and oriented along the longitudinal dimension of the component with alignment normal or perpendicular to that dimension also possible. The fibers may be of uniform or random length, unidirectional or multidirectional and may be as short as about 3 to about 4 millimeters (mm) or shorter. Due to the improved structural integrity, the amount of fibers in the structural component preferably equals at least about 20% by weight (wt %) and preferably about 20 wt % to about 70 wt %. Possible reinforcing fibers, which are preferably used in accordance with U.S. Pat. Nos. 4,717,341 and 4,894,012 to Goldberg et al. (which are herein incorporated by reference), include glass, carbon, graphite, polyaramid, mixtures thereof, as well as other fibers known in the art.

In order to enhance the bond between the fibers and polymeric matrix, thereby enhancing the reinforcing effect, the fibers may be silanized or otherwise treated such as by grafting functional monomers to obtain proper coupling between the fibers and the resin matrix. Silanization renders the fibers hydrophobic, reducing the water sorption and improving the hydrolytic stability of the composite material, renders the fibers organophilic, improving wetting and mixing, and bonds the fibers to the polymeric matrix. Typical silane is A-174 (p-methacrylate propyl tri-methoxy silane), produced by OSI Specialties, New York.

The polymeric matrix is selected from those known in the art of dental materials, including, but not limited to, polyamides, polyesters, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates (hereinafter abbreviated to PUDMA), and the like. Preferred polymeric matrix materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. Nos. 5,276,068 to Waknine (which are herein incorporated by reference). An especially preferred methacrylate monomer is the condensation product of bisphenol A and glycidyl methacrylate, 2,2'-bis [4-(3-methacryloxy-2-hydroxy propoxy)-phenyl]-propane (hereinafter abbreviated "BIS-GMA").

The polymer matrix, which typically includes polymerization initiators, polymerization accelerators, ultra-violet light absorbers, anti-oxidants, fluorescent whitening agents, free radical initiators, and/or other additives well known in the art, may be visible light curable, self-curing, dual curing, or vacuum, heat, or pressure curable compositions, as well as any combination thereof. Heat and pressure or vacuum curable compositions include a heat cure initiator such as benzoyl peroxide, 1,1'-azobis(cyclohexanecarbo-nitrile) or other free radical initiators. The preferred polymeric matrix is a light and heat curable matrix, wherein light effects partial cure of the polymer matrix, while final curing is by heat under controlled atmosphere.

The structural component may further include up to about 30 wt % of one or more fillers known in the art and used in dental restorative materials, with the specific amount of such filler being determined by the particular use of the composite material. Suitable fillers include those capable of being covalently bonded to the polymeric matrix itself or to a coupling agent that is covalently bonded to both. Fillers include silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania, among other conventional fillers such as those disclosed in commonly assigned U.S. Pat. Nos. 4,544,359 and 4,547,531 to Waknine (which are incorporated herein by reference), while possible coupling agents include silanes, zirconates and titanates.

Although the structural component may be formed from the fibers and polymeric matrix by the dentist or technician and then shaped into the required structural component, the fibers are preferably intimately mixed with the polymeric matrix, for example by compression molding or pultrusion, and either provided to the dentist or technician in this form for ultimate shaping or formed into the ultimate shape and provided to the dentist or technician for use.

Referring to FIG. 1, a first embodiment of the method of the present invention is shown, wherein the fiber-reinforced composite structural component is in the form of a reinforcing bar 12 providing structural support for the bridge between abutment teeth 14, 16. The cross section of reinforcing bar 12 may be rectangular, rhomboidal, ovoidal, cylindrical, or of any other cross-sectional configuration effective to provide strength, stiffness, and structural integrity to the finished bridge.

Formation of the bridge using reinforcing bar 12 first requires preparation of the abutment teeth 14, 16. Preparation is similar to typical shoulder preparations for full coverage bridges, i.e. 90°–100° cavosurface angle with approximately 1.0 mm axial reduction and 1.5 mm occlusal reduction. Where desired, interproximal boxes 20, 22, such as small (2 mm×2 mm×2 mm) boxes, are cut into abutment teeth 14, 16, after the normal preparation is completed, thereby providing a space to rest reinforcing bar 12. While the boxes are preferred, ledges, rest platform(s), indentations or cavities of any geometry capable of holding reinforcing bar 12 in place may be used, with the size of the box dictated by the size of the reinforcing bar and other considerations such as the age of the teeth. (Younger teeth with a large pulp chamber will require preparation of a smaller box.)

Once the abutment teeth 14, 16, have been prepared with interproximal cavities 20, 22, a negative impression of the abutment teeth 14, 16, including the interproximal cavities 20, 22, and the space therebetween, is made by conventional methods. A positive model or die (FIG. 1B) is then formed from the negative impression and utilized to form the reinforcing bar 12.

Where the interproximal boxes 20, 22, are used, a thin layer (0.3–0.5 mm) of opacious dentin composite resin (i.e., up to about 95 wt % filler dispersed in polymeric matrix) is preferably applied to the trimmed and prepared die and cured (FIG. 1A) prior to the application of the reinforcing bar 12. The overlay particulate composite, commonly referred to as veneer (i.e., up to about 95 wt % filler dispersed in polymeric matrix), which protects the fibers in the reinforcing bar from potential exposure or damage due to future dental work and protects the teeth and gums from possible irritation, can be obtained from Jeneric/Pentron, Inc., Wallingford, Conn., under the trademarks SCULPTURES® and FLOW-IT®.

Where a box is not desirable, a negative impression and positive model or die are similarly made of the prepared teeth, the dentin composite resin is similarly applied and cured, and then additional dentin composite resin is used to build up a rest platform 28 on the mesial and distal side of the abutment teeth, 14, 16, respectively, below the contact area, and the resin is cured (see FIG. 2).

The longest distance above the edentulous area between the two facing walls (mesial and distal) of the prepared interproximal boxes 14, 16, is then measured and the reinforcing bar 12 is then fabricated. The bar should have a length, width, and height sufficient to span the measured distance, remain supported in the interproximal boxes, and impart the desired structural integrity to the pontic, enabling it to withstand the stresses associated with mastification. The reinforcing bar 12 may be provided to the dentist or technician as a prefabricated composite or it may be fabricated by the dentist or technician from fibers described and an appropriate polymeric matrix. In a particularly preferred embodiment, the fiber-reinforced composite material is supplied to the dentist or technician in the form of a ribbon with the fibers preimpregnated with uncured polymeric matrix. This form is easy for the dentist or technician to manipulate and form into the required shapes, since the composite material retains a degree of malleability.

Typically, forming a reinforcing bar of this composite material, comprises cutting several lengths of ribbon of the required length. Sufficient cuttings are then preferably pressed together, via rolling or other appropriate means, so as to attain the desired size and geometry structural component, to eliminate voids, and to place the individual strips in intimate contact. Alternatively, multiple strips may be placed in the interproximal boxes or on the platform and pressed together.

The reinforcing bar(s) may be merely placed directly in the interproximal boxes or on the platforms, or a small amount of uncured or partially cured tacky resin, special resin FLOW-IT® (Jeneric/Pentron, Inc.) may be used to hold the reinforcing bar(s) in place. For ease in forming the pontic, the reinforcing bars are then preferably partially cured, which results in stiffening. A pontic may then be placed or built up around the bar using methods known in the art.

Referring now to FIG. 2, wherein the fiber-reinforced composite structural component includes an occlusal strip 20 which provides structural support for the reinforcing bar 12 between abutment teeth 14, 16. Occlusal strip 20 is formed by measuring the maximum distance between the mesial and distal sides of teeth 14, 16, and forming a strip of ribbon having that length. Preferably occlusal strip 20 is placed on the occlusal face 22 of one tooth, pushed into place so as to eliminate voids. The remainder of the occlusal strip 20 is then pushed into place on the occiusal face 24 of the remaining abutment tooth. Additional fiber-strips can be placed on the lingual, buccal/labical, and cervical sides of the structural bar in the edentulous area for proper support of the overlay sculpting material. A pontic may then be placed or built up around the bar using methods known in the art. As the occlusal strip is attached to the abutment teeth it may be cured or partially cured for ease of handling. For example, after the occlusal strip 20 is attached to the occlusal face 22, that portion of the strip may be cured prior to attaching the strip to the occlusal face 24.

Referring now to FIG. 3, the wrap 30 is wrapped around at least one of the abutment teeth 14, 16. Particulate filler composite (i.e., up to 95% filler dispersed in polymeric matrix) is placed at site 32 and the corresponding site on the opposite side of the tooth to be wrapped preferably in order to assist in the adhesion of the ribbon during wrapping, and to inhibit void formation. If reinforcing bar 12 is in place as shown, tacky resin 34 is placed on the side 36 of the reinforcing bar 12 to aid adherence of the wrap. Preferably, the wrap 30 is formed by measuring the length from the distal side of the first tooth 14 to the distal side of the second tooth 16. A length of strip is cut equal to twice the measured length plus about 5 mm, and a first end of the ribbon is adhered to the reinforcing bar 12 at point 46. The strip is then pushed intimately against the bar so as to eliminate voids. For ease of handling, the attached section of the wrap 30 is adhered to the bar by either partially curing that section or by holding the section to the bar using clamp(s). The ribbon is then wrapped around tooth 14 so as to form an intimate and void-free seal. That section of the ribbon can also be partially cured. Finally, the ribbon is pushed against the other side of the reinforcing bar 12, and either also partially cured or placed under the clamps. If clamp(s) are employed, the wrap may optionally be partially cured before application of a pontic. A pontic may then be placed or built up around the reinforcing bar 12 using methods known in the art and materials such as particulate filler composite. Upon cure, the wrap forms a structural support.

In addition to employing the wrap to wrap abutment teeth and a bar, the wrap and/or occlusal strip can be used on a single broken tooth to provide structural support thereof, prior to forming a pontic thereon, i.e., to form a crown. The occlusal strip is preferably either applied before the wrap such that the wrap covers the edges of the occlusal strip, preventing de-attachment thereof, or is integral with the wrap such that the wrap forms the occlusal strip.

Referring now to FIG. 4, an inlay or onlay bridge and method of forming according to the present invention is shown, wherein at least one reinforced structural component, in the form of a bar 42, provides structural support for a bridge between abutment teeth 14, 16. The ends of the strip are being spread to cover the occlusal floor.

Figure 1A:
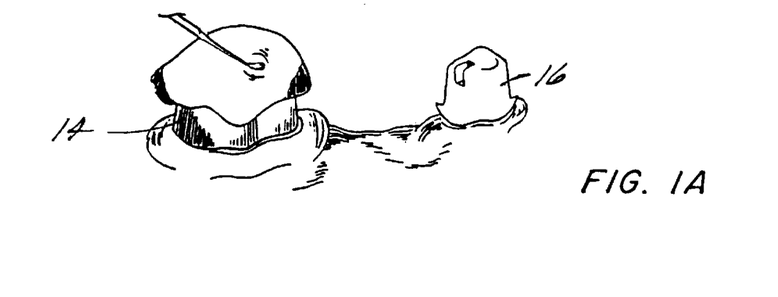
FIG. 1 shows a sequence of steps in forming a three-unit full coverage bridge comprising at least one fiber-reinforced structural component in the form of a bar in accordance with one embodiment of the present invention.
Figure 1B:
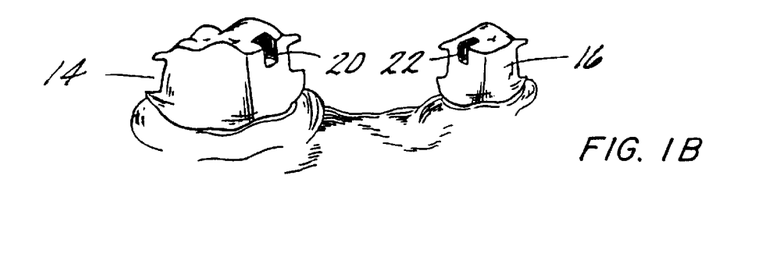
Figure 1C:
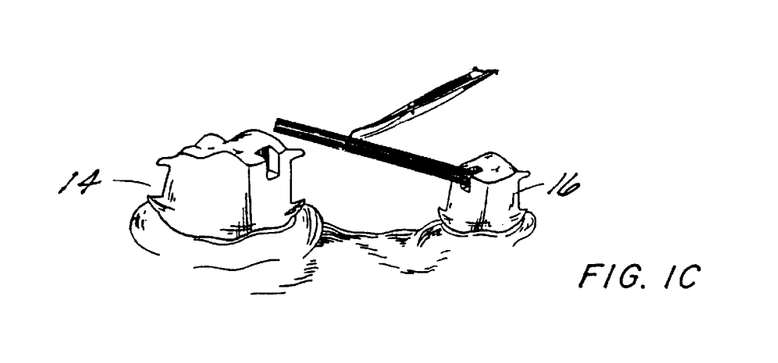
Figure 1D:
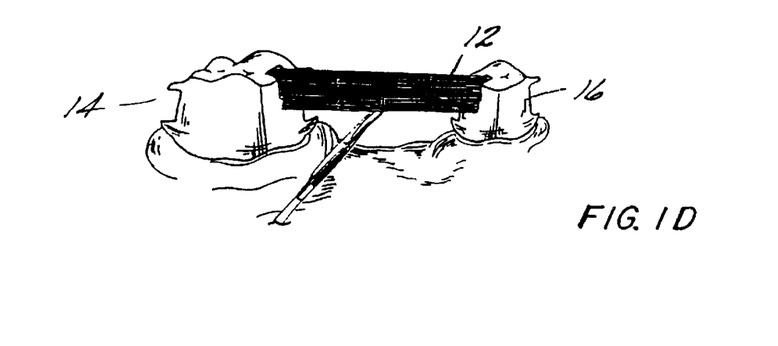
Figure 2A:
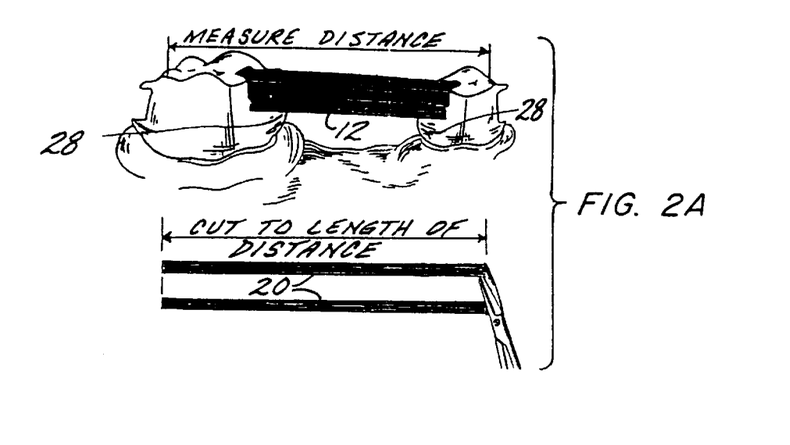
FIG. 2 shows a sequence of steps in forming a three-unit full coverage bridge comprising at least one fiber-reinforced structural component in the form of a bar and an occlusal strip in accordance with another embodiment of the present invention.
Figure 2B:
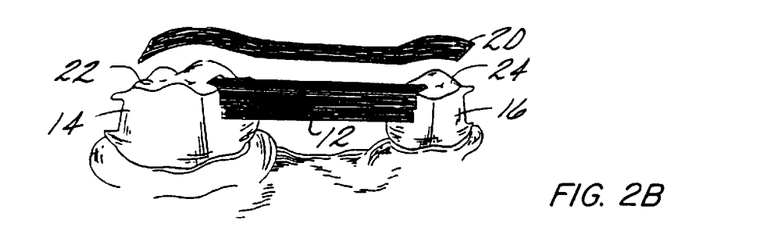
Figure 2C:
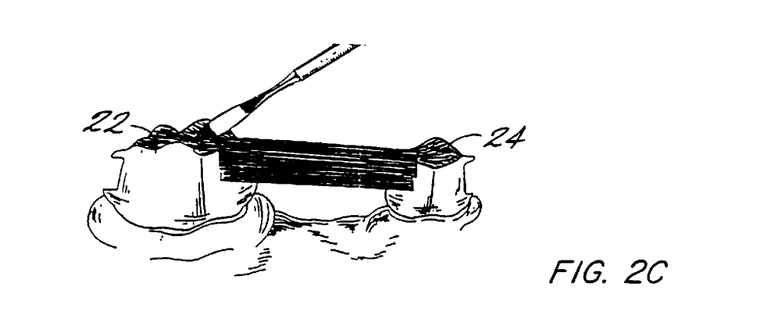
Figure 2D:
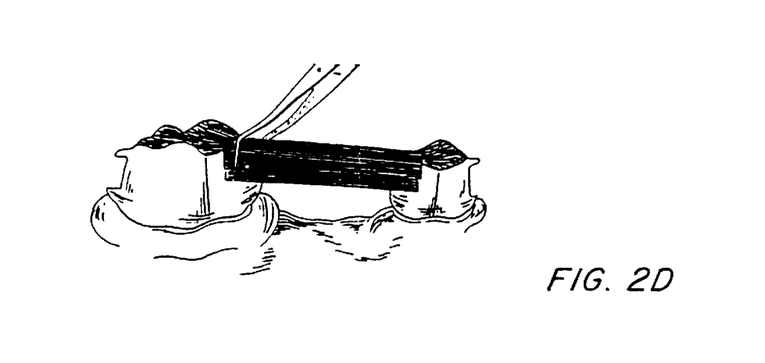
Figure 3A:
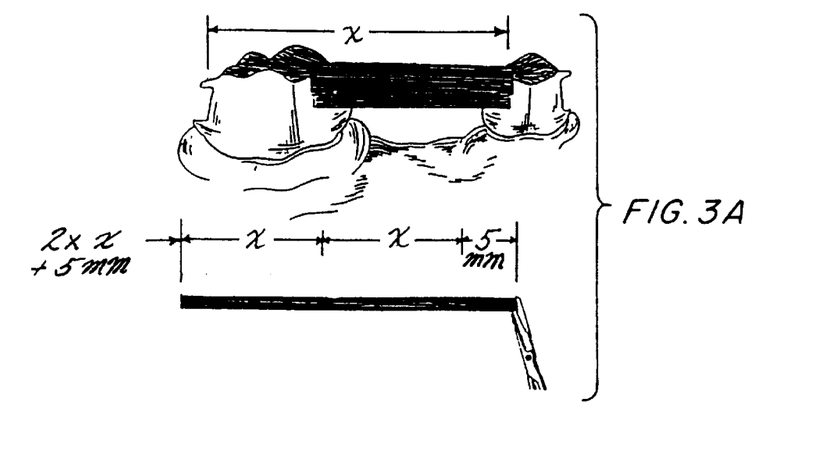
FIG. 3 shows a sequence of steps in forming a three-unit full coverage bridge comprising at least one fiber-reinforced structural component in the form of a bar and an occlusal strip in accordance with a third embodiment of the present invention.
Figure 3B:
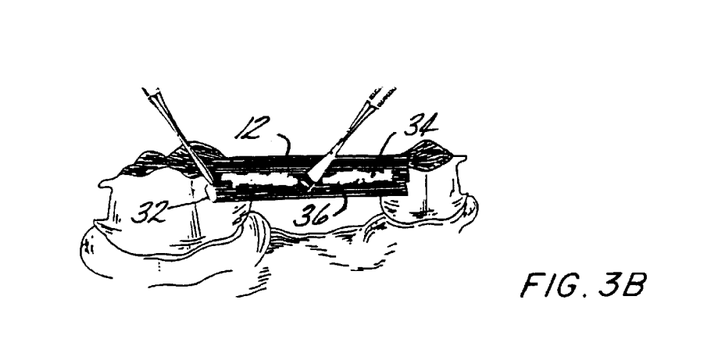
Figure 3C:
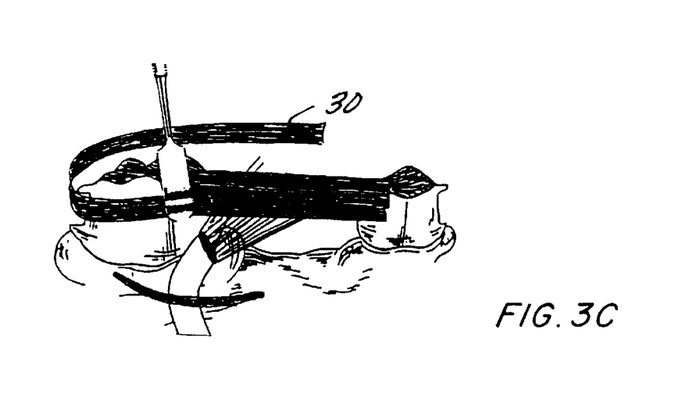
Figure 3D:
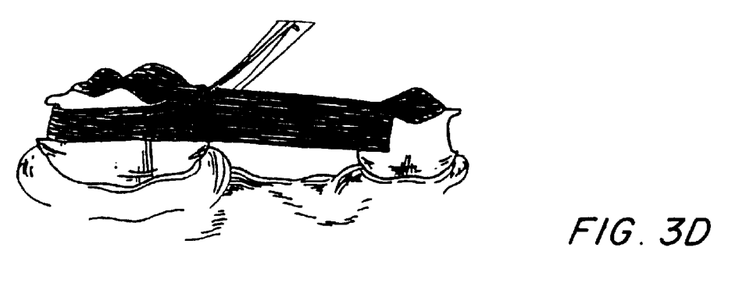
Figure 3E:
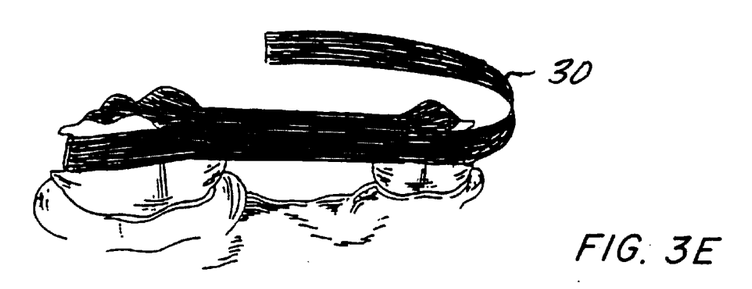
Figure 3F:
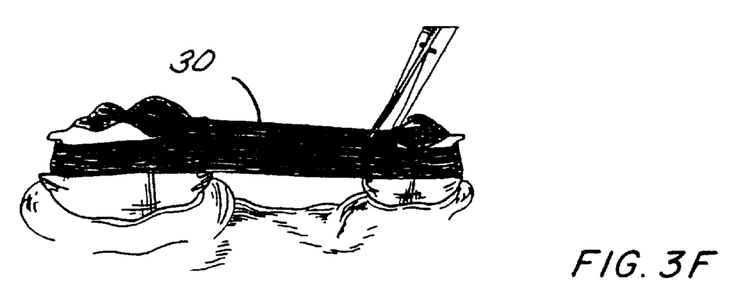
Figure 4A:
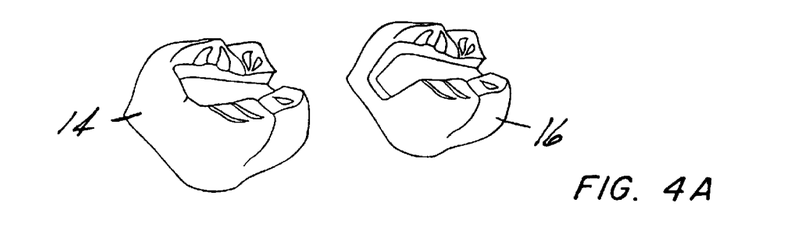
FIG. 4 shows a sequence of steps in forming an inlay bridge comprising at least one fiber-reinforced structural component in the form of a bar in accordance with a fourth embodiment of the present invention.
Figure 4B:
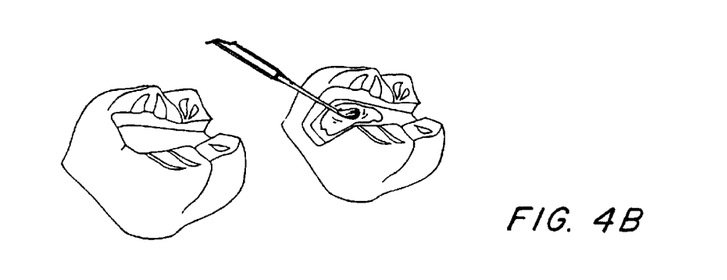
Figure 4C:
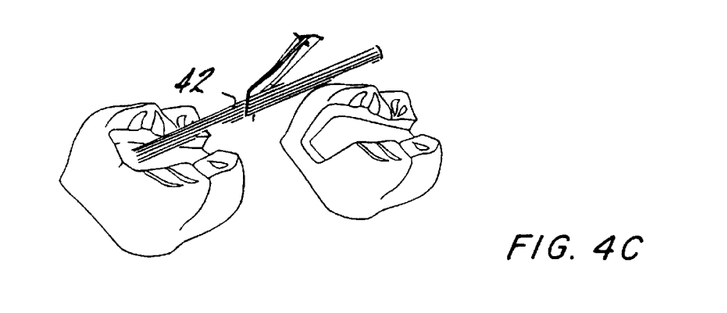
Figure 4D:
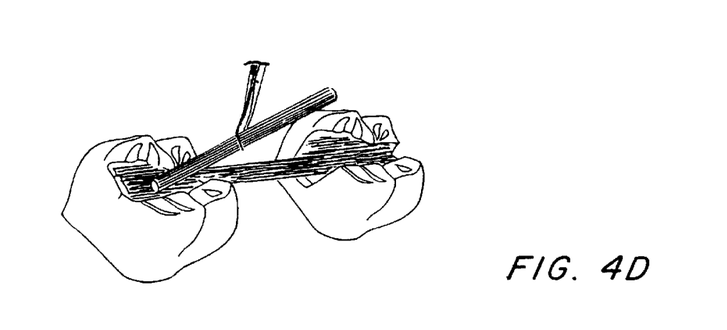
Figure 5:
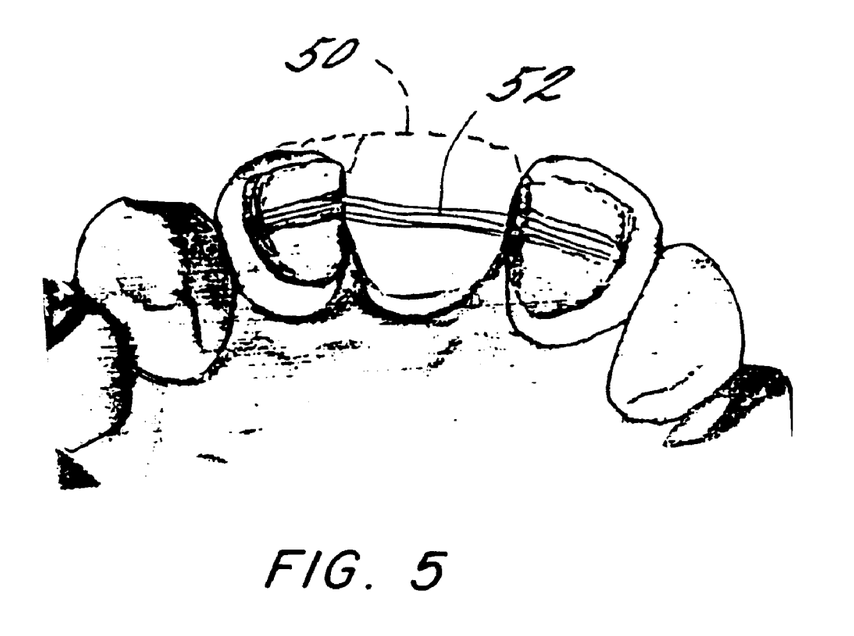
FIG. 5 shows a perspective view, partially in section, of a winged bridge comprising at least one fiber-reinforced structural component in the form of a bar in accordance with a fifth embodiment of the present invention.
Figure 6A:
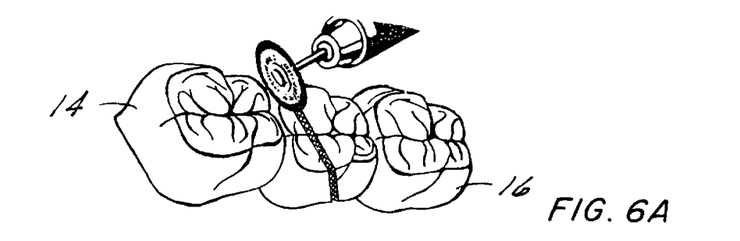
FIG. 6 shows a sequence of steps in forming a bridge repair comprising at least one fiber-reinforced structural component in the form of a bar in accordance with yet another embodiment of the present invention.
Figure 6B:
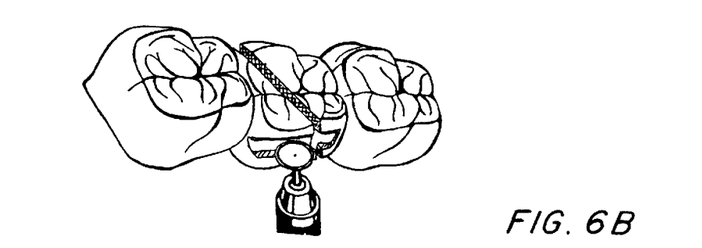
Figure 6C:
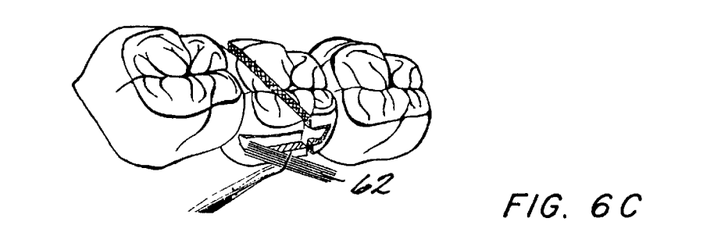
Figure 6D:
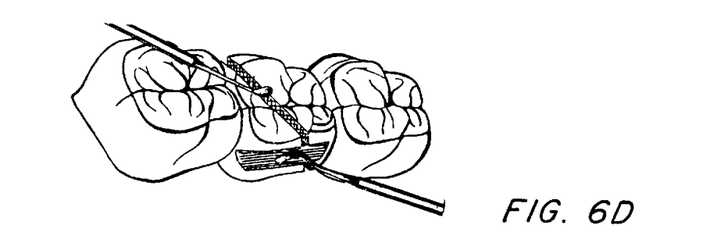
Figure 6E:
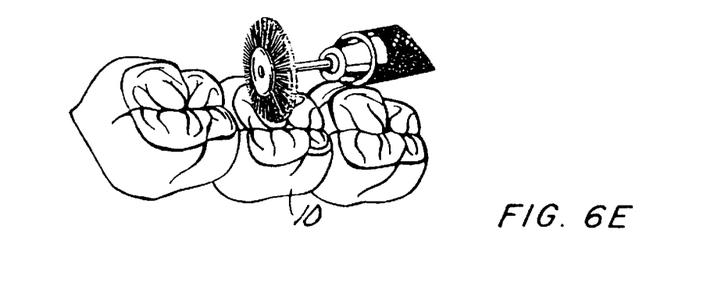

In another embodiment of the present invention a "winged" or Maryland bridge 50 is formed comprising a fiber-reinforced structural component in the form of a bar 52 providing structural support for the bridge as shown in FIG. 5. Such bridges are described in U.S. Pat. No. 5,000,687. The bar 52 is placed so as to reinforce the wing portions and the pontic by methods similar to that described above for the inlay or onlay bridges. Enough room must be left to completely cover the fiber-reinforced composite component with particulate-filled composite.

Referring now to FIG. 6, a fiber-reinforced structural component, in the form of strip 62, provides structural support for repair of a bridge having pontic 10 between abutment teeth 14, 16. To repair the bridge, which has been sectioned to provide better fit, for example, the bridge is first sectioned with a thin diamond disk preferably diagonally through the pontic 10, the cut being no more than 1 mm in width (FIG. 6A). Lingual grooves are then cut through the entire length of the pontic 10, preferably 3 to 4 mm in depth (FIG. 6B). The sectioned pieces are then cleaned, for example ultrasonically, and the bridge segments replaced on a new model in the correct relationship. A thin coat of a thinning liquid (Jeneric/Pentron, Inc.), silane, flowable composite, or unfilled bonding adhesive is applied to the internal surfaces of the grooves and diagonal cuts to assist wetting. Appropriate lengths of strip 62 are forced into the grooves, and any excess resin is removed. The repaired pontic is partially light cured from both the lingual and the labial (buccal) side, and then completely cured. After complete curing, the buccal (labial) surface is cut back in order to allow the addition of composite resin material to completely cover the fiber-reinforced composite and to restore acceptable contouring to the pontic.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A process for forming a dental restoration, using at least two abutment teeth each having an occlusal portion, comprising the steps of:

forming opposing first and second interproximal cavities in the distal occlusal portion of the mesial abutment tooth and in the mesial occlusal portion of the distal abutment tooth, respectively;

preparing at least one structural component comprising reinforcing fibers embedded within a polymeric matrix, said component having a sufficient size and geometry to span in and between said first interproximal cavity and said second interproximal cavity;

disposing the structural component in and between the first and second interproximal cavities; and attaching an occlusal strip to the occlusal portion of one of said abutment teeth and to said structural component, said occlusal strip comprising second reinforcing fibers embedded within a second polymeric matrix.

2. The process for forming a dental restoration as in claim 1, wherein attaching said occlusal strip comprises the steps of:

attaching a first portion of said occlusal strip to the occlusal portion of said one of said abutment teeth;

partially curing said first portion;

attaching a second portion of said occlusal strip to said structural component and partially curing said second portion;

attaching a third portion of said occlusal strip to the occlusal portion of another of said abutment teeth; and partially curing said third portion.

3. The process for forming a dental restoration as in claim 1, further comprising the steps of:

taking an impression of said abutment teeth and interproximal cavities, wherein a model is prepared from said impression;

applying a composite resin to said model.

4. The process for forming a dental restoration as in claim 1, further comprising curing said structural component and said occlusal strip.

5. The process of forming a dental restoration as in claim 1, wherein the polymeric matrix is uncured or partially cured.

6. The process of forming a dental restoration as in claim 1, wherein said structural component is in the form of an elongated member and said fibers embedded within said polymeric matrix are at least partially aligned and orientated along a longitudinal dimension of said elongated member.

7. The process of forming a dental restoration as in claim 1, wherein the fiber-reinforced composite structural component has a cross-sectional shape effective to provide strength, stiffness, and structural integrity to the dental restoration.

8. The process of forming a dental restoration as in claim 7, wherein the cross-sectional shape is essentially rectangular, rhomboidal, ovoidal or cylindrical.

9. The process of forming a dental restoration as in claim 1, wherein said structural component is in the form of a pre-formed ribbon, with said reinforcing fibers impregnated with uncured polymeric matrix.

10. A process of forming a dental restoration, using at least two abutment teeth each having mesial and distal occlusal portions, comprising the steps of:

forming opposing first and second interproximal cavities in the distal occlusal portion of the mesial abutment tooth and in the mesial occlusal portion of the distal abutment tooth, respectively;

preparing a model to prepare at least one structural component comprising reinforcing fibers embedded within a polymeric matrix, said structural component having a sufficient size and geometry to span in and between said first interproximal cavity and said second interproximal cavity; and disposing said structural component in and between the first and second interproximal cavities;

forming a wrap having an end;

attaching the end of said wrap to a first side of said structural component; and wrapping a first portion of said wrap around at least a portion of one of said abutment teeth.

11. The process of forming a dental restoration as in claim 10, further comprising attaching said wrap to a first side of said structural component.

12. The process of forming a dental restoration as in claim 11, further comprising:

wrapping said wrap around at least a portion of another of said abutment teeth.

13. The process of forming a dental restoration as in claim 12, further comprising:

attaching said wrap to a second side of said structural component opposing said first side.

14. The process of forming a dental restoration as in claim 13, further comprising:

repeating steps of wrapping until said abutment teeth and structural component have achieved sufficient structural integrity to endure forces associated with mastication.

15. A process of forming a dental restoration as in claim 13, further comprising holding said wrap on said structural component with at least one clamp.

16. A process of forming a dental restoration as in claim 11, further comprising holding said wrap on said structural component with at least one clamp.

17. The process of forming a dental restoration as in claim 11, further comprising:

partially curing said end of said wrap prior to wrapping said wrap; and partially curing said first portion of said wrap.

18. The process of forming a dental restoration as in claim 10, wherein said wrap has a length of about twice a distance from the distal side of the first abutment tooth to the distal side of the second abutment tooth plus about 5 millimeters.

19. The process of forming a dental restoration as in claim 10, wherein the polymeric matrix is uncured or partially cured.

20. The process of forming a dental restoration at in claim 10, wherein said structural component is in the form of an elongated member and the fibers embedded within the polymeric matrix are at least partially aligned and orientated along the longitudinal dimension of the elongated member.

21. The process of forming a dental restoration as in claim 10, wherein the fiber-reinforced structural component has a cross-sectional shape effective to provide strength, stiffness, and structural integrity to the dental restoration.

22. The process of forming a dental restoration as in claim 21, wherein the cross-sectional shape is essentially rectangular, rhomboidal, ovoidal or cylindrical.

23. The process of forming a dental restoration as in claim 10, wherein said structural component is in the form of a pre-formed ribbon, with the reinforcing fibers impregnated with uncured polymeric matrix.

24. A process for forming a dental restoration, using at least two abutment teeth each having an occlusal portion, comprising the steps of:

forming opposing first and second interproximal cavities in the distal occlusal portion of the mesial abutment tooth and in the mesial occlusal portion of the distal abutment tooth, respectively;

preparing at least one uncured structural component comprising reinforcing fibers embedded within uncured polymeric matrix, said structural component having a sufficient size and geometry to span in and between said first interproximal cavity and said second interproximal cavity;

disposing said uncured structural component in and between the first and second interproximal cavities; and curing the structural component.

25. The process for forming a dental restoration as in claim 24, wherein said first and second interproximal cavities have a sufficient depth and geometry to support said structural component.

26. The process for forming a dental restoration as in claim 24, wherein said first and second interproximal cavities are formed above the cervical area of said abutment teeth.

27. The process for forming a dental restoration as in claim 24, further comprising the steps of:

taking an impression of the abutment teeth and interproximal cavities, wherein a model is prepared from said impression; and applying a dentin composite to said model.

28. The process of forming a dental restoration as in claim 24, wherein said structural component is in the form of an elongated member and the fibers embedded within the polymeric matrix are at least partially aligned and orientated along the longitudinal dimension of the elongated member.

29. The process of forming a dental restoration as in claim 24, wherein said structural component has a cross-sectional shape effective to provide strength, stiffness, and structural integrity to the dental restoration.

30. The process of forming a dental restoration as in claim 29, wherein the cross-sectional shape is essentially rectangular, rhomboidal, ovoidal or cylindrical.

31. A process for forming a dental restoration as in claim 24, further comprising:

forming a pontic on said structural component; and curing said pontic.

32. A dental bridge for replacing at least one missing natural tooth in which first and second abutment teeth have opposing first and second interproximal cavities in the distal portion of the occlusal surface of the mesial abutment tooth and in the mesial occlusal surface of the distal abutment tooth, respectively, comprising:

at least one structural component comprising reinforcing fibers embedded within a polymeric matrix, said structural component formed to span in and between the first and second interproximal cavities of the abutment teeth; and a wrap having second reinforcing fibers embedded within a second polymeric matrix, said wrap attached to said structural component and configured to be attached to at least one of said abutment teeth.

33. A dental bridge as in claim 32, wherein said wrap is an occlusal strip configured to be attached to the occlusal surface of at least one of said abutment teeth.

34. A dental bridge as in claim 33, wherein said wrap is configured to be attached to at least a portion of a side of said first and said second abutment teeth.

35. A dental bridge as in claim 32, wherein said wrap is configured attached to at least a portion of a side of said first and said second abutment teeth.

36. A dental bridge as in claim 32, wherein said structural component is in the form of an elongated member and the fibers embedded within the polymeric matrix are at least partially aligned and orientated along a longitudinal dimension of said elongated member.

37. A dental bridge as in claim 32, wherein said structural component has a cross-sectional geometry which provides strength, stiffness and structural integrity to the bridge.

38. A dental bridge as in claim 37, wherein the cross-sectional shape is essentially rectangular, rhomboidal, ovoidal, or cylindrical.

39. A dental crown, comprising:

a wrap having reinforcing fibers embedded within polymeric matrix configured to be wrapped around and attached to at least a portion of a natural tooth.

40. A dental crown as in claim 39, wherein said wrap has a portion which forms an occlusal strip configured to be attached to an occlusal portion of said at least a portion of natural tooth.

41. A dental crown as in claim 39, further comprising an occlusal strip having an edge, said at least a portion of occlusal strip configured attached to an occlusal portion of said natural tooth.

42. A dental crown as in claim 41, wherein said wrap intimately contacts and covers said occlusal strip edge.

43. A dental crown as in claim 41, further comprising coating said occlusal strip and wrap with veneer.

44. A method for forming a dental crown, comprising the steps of:

wrapping a wrap around a damaged natural tooth, and wrap comprising intimately contacting said natural tooth with sad wrap, fibers embedded within a polymeric matrix.

45. A method for forming a dental crown as in claim 44, further comprising wrapping said wrap around said natural tooth such that at least a portion of said wrap protrudes above an occlusal surface of said natural tooth; and adhering said protruding portion to said occlusal surface.

46. A method for forming a dental crown as in claim 44, further comprising disposing an occlusal strip having fibers embedded within a polymeric matrix on an occlusal surface of said natural tooth.

47. A method for forming a dental crown as in claim 46, further comprising disposing said occlusal strip prior to wrapping said tooth such that said wrap covers an edge of said occlusal strip.

* * * * *

UNITED STATES PATENT AND TRADEMARK OFFICE
CERTIFICATE OF CORRECTION

PATENT NO. : 6,039,569
DATED : March 21, 2000
INVENTOR(S) : Arun Prasad et al.

It is certified that error appears in the above-identified patent and that said Letters Patent is hereby corrected as shown below:

Column 4,
Line 59, after "trademarks" delete "SCULPTURES®" and insert therefor
-- SCULPTURE® --

Column 5,
Line 46, after "the" delete "occiusal" and insert therefor -- occlusal --

Column 10,
Line 12, after "configured" insert -- to be --
Line 28, after "to" delete "at least a portion of"
Line 34, after "said" delete "at least a portion of"
Line 35, after "configured" insert -- to be --
Line 36, delete "said"
Line 44, delete "wrap comprising"
Line 45, after "with" delete "sad" and insert therefor -- said --
Line 45, after "wrap," insert -- said wrap comprising --

Signed and Sealed this

Thirtieth Day of March, 2004

JON W. DUDAS
*Acting Director of the United States Patent and Trademark Office*